(12) United States Patent
Beckham et al.

(10) Patent No.: US 10,266,852 B2
(45) Date of Patent: Apr. 23, 2019

(54) LIGNIN CONVERSION TO FUELS, CHEMICALS AND MATERIALS

(71) Applicants: Alliance for Sustainable Energy, LLC, Golden, CO (US); The Board of Trustees of the University of Illinois, Urbana, IL (US)

(72) Inventors: Gregg T. Beckham, Denver, CO (US); Jeffrey G. Linger, Denver, CO (US); Derek R. Vardon, Lakewood, CO (US); Michael T. Guarnieri, Denver, CO (US); Eric M. Karp, Lakewood, CO (US); Mary Ann Franden, Centennial, CO (US); Christopher W. Johnson, Denver, CO (US); Timothy J. Strathmann, Champaign, IL (US); Philip T. Pienkos, Lakewood, CO (US)

(73) Assignees: Alliance for Sustainable Energy, LLC, Golden, CO (US); The Board of Trustees of the University of Illinois, Urbana, IL (US)

( * ) Notice: Subject to any disclaimer, the term of this patent is extended or adjusted under 35 U.S.C. 154(b) by 236 days.

(21) Appl. No.: 14/563,299

(22) Filed: Dec. 8, 2014

(65) Prior Publication Data
US 2018/0371502 A1 Dec. 27, 2018

Related U.S. Application Data

(60) Provisional application No. 61/912,826, filed on Dec. 6, 2013.

(51) Int. Cl.
| | |
|---|---|
| *C12Q 1/18* | (2006.01) |
| *C12P 5/02* | (2006.01) |
| *C12P 7/62* | (2006.01) |
| *C12P 7/42* | (2006.01) |
| *C12P 5/00* | (2006.01) |

(52) U.S. Cl.
CPC ............ *C12P 5/02* (2013.01); *C12P 5/002* (2013.01); *C12P 7/42* (2013.01); *C12P 7/625* (2013.01)

(58) Field of Classification Search
CPC .... B01D 2311/2688; C12P 7/10; C12P 19/14; C12P 19/02; C12P 2201/00; C12P 7/06; C12P 7/14; Y02E 50/16; Y02E 50/13; Y02E 50/343; C12M 21/12; D21C 5/005; C02F 11/04; C02F 3/34; C13K 13/002; C13K 13/00; C13K 1/02; C12N 9/2445
IPC .............. C02F 11/04,3/34; C12P 19/14, 19/02, 2201/00, 7/06, 7/10, 7/14; C13K 13/00, 13/002, 1/02; B01D 2311/2688; C12M 21/12; D21C 5/005; Y02E 50/16, 50/13, 50/343; C12N 9/42
See application file for complete search history.

(56) References Cited

U.S. PATENT DOCUMENTS

| | | | |
|---|---|---|---|
| 1,594,389 A | 8/1926 | Thellier | |
| 1,888,025 A | 11/1932 | Bent | |
| 2,037,001 A | 4/1936 | Aronovsky | |
| 2,042,705 A | 6/1936 | Dreyfus | |
| 3,888,727 A * | 6/1975 | Kenig | D21C 3/263 |
| | | | 162/65 |
| 3,932,207 A | 1/1976 | Fogarassy | |
| 4,259,444 A | 3/1981 | Chakrabarty | |
| 4,480,034 A | 10/1984 | Hsieh | |
| 4,520,105 A | 5/1985 | Sinner et al. | |
| 4,594,130 A | 6/1986 | Chang et al. | |
| 4,731,328 A | 3/1988 | Maxwell | |
| 5,487,987 A | 1/1996 | Frost et al. | |
| 5,730,837 A | 3/1998 | Black et al. | |
| 6,426,438 B1 * | 7/2002 | Fischer | C07C 29/149 |
| | | | 568/864 |
| 8,133,704 B2 | 3/2012 | Baynes et al. | |
| 8,211,683 B2 | 7/2012 | Mase et al. | |
| 9,206,445 B2 * | 12/2015 | Yang | C12P 7/065 |
| 2014/0107381 A1 | 4/2014 | Beckham et al. | |
| 2014/0186902 A1 | 7/2014 | Botes et al. | |
| 2014/0193868 A1 | 7/2014 | Sabirova et al. | |
| 2014/0273104 A1 * | 9/2014 | Paripati | C12P 19/14 |
| | | | 435/99 |
| 2014/0302573 A1 | 10/2014 | Burk et al. | |
| 2016/0017381 A1 | 1/2016 | Beckham et al. | |
| 2016/0052949 A1 | 2/2016 | Beckham et al. | |
| 2017/0275655 A1 | 9/2017 | Beckham et al. | |

FOREIGN PATENT DOCUMENTS

| | | |
|---|---|---|
| WO | WO 2011/017560 A1 | 2/2011 |
| WO | WO 2012/106257 A1 | 8/2012 |

OTHER PUBLICATIONS

Kim et al. 1999. PHAs Produced by Pseudomonas putida and Pseudomonas oleovorans Grown with n-Alkanoic Acids Containing Aromatic Groups. Macromolecules vol. 32, pp. 6058-6064.*
Lee et al., 2000. Enzyme & Microbial Technology, vol. 27, pp. 33-36. (Year: 2000).*
Keenan et al. "Polyhydroxyalkanoate copolymers from forest biomass" J Ind Microbiol Biotechnol (2006) 33: 616-626 (Year: 2006).*
Alén et al., "Gas-liquid Chromatographic Separation of Hydroxy Monocarboxylic Acids and Dicarboxylic Acids on a Fused-silica Capillary Column", Journal of Chromatography A, 1984, vol. 301, pp. 273-276.
Alonso et al., "Bimetallic Catalysts for Upgrading of Biomass to Fuels and Chemicals", Chemical Society Reviews, 2012, vol. 41, pp. 8075-8098.

(Continued)

*Primary Examiner* — Thane Underdahl
(74) *Attorney, Agent, or Firm* — Michael A. McIntyre

(57) ABSTRACT

Disclosed herein are methods for the production of fuels, chemicals, or materials from biomass-derived lignin, cellulose, and hemicellulose. Also provided are methods for the production of polyhydroxyalkanoates from lignocellulosic biomass and the subsequent thermal and catalytic conversion of polyhydroxyalkanoates to hydrocarbons. In addition, methods for the production of ethanol from the fermentation of polysaccharides are described.

16 Claims, 12 Drawing Sheets

(56) References Cited

OTHER PUBLICATIONS

Bang et al., "DO-Stat Fed-Batch Production of cis, cis-Muconic Acid from Benzoic Acid by Pseudomonas putida BM014", Journal of Fermentation and Bioengineering, 1995, vol. 79, No. 4, pp. 381-383.
Bechthold et al., "Succinic Acid: A New Platform Chemical for Biobased Polymers from Renewable Resources", Chemical Engineering and Technology, May 2008, vol. 31, No. 5, pp. 647-654.
Bonawitz et al., "Disruption of Mediator Rescues the Stunted Growth of a Lignin-deficient *Arabidopsis* Mutant", Nature, May 2014, vol. 509, pp. 376-380.
Bozell et al., "Solvent fractionation of renewable woody feedstocks: Organosolv generation of biorefinery process streams for the production of biobased chemicals", Biomass and Bioenergy, 2011, vol. 35, pp. 4197-4208.
Chen et al., "Lignin Modification Improves Fermentable Sugar Yields for Biofuel Production", Nature Biotechnology, Jul. 2007, vol. 25, No. 7, pp. 759-761.
Chundawat et al., "Deconstruction of Lignocellulosic Biomass to Fuels and Chemicals", Annual Reviews Chemical and Biomolecular Engineering, 2011, vol. 2, pp. 121-145.
Ciesielski et al., "Engineering Plant Cell Walls: Tuning Lignin Monomer Composition for Deconstructable Biofuel Feedstocks or Resilient Biomaterials", Green Chemistry, 2014, vol. 16, pp. 2627-2635.
Dabrowski et al., "Adsorption of Phenolic Compounds by Activated Carbon—A Critical Review", Chemosphere, 2005, vol. 58, pp. 1049-1070.
Davis et al., "Process Design and Economics for the Conversion of Lignocellulosic Biomass to Hydrocarbons: Dilute-acid and Enzymatic Deconstruction of Biomass to Sugars and Biological Conversion of Sugars to Hydrocarbons", NREK Technical Report NREL/TP-5100-60223, Oct. 2013, pp. 1-147.
de Boer et al., "The tac promoter: A functional hybrid derived from the trp and lac promoters", Proceedings of the National Academy of Sciences of the United States of America, Jan. 1983, vol. 80, pp. 21-25.
Van de Vyver et al., "Emerging Catalytic Processes for the Production of Adipic Acid", Catalysis Science & Technology, 2013, vol. 3, pp. 1465-1479.
Draths et al., "Environmentally Compatible Synthesis of Adipic Acid from D-glucose", Journal of the American Chemical Society, 1994, vol. 116, No. 1, pp. 399-400.
Fort et al., Green Chemistry, "Can Ionic Liquids Dissolve Wood? Processing and Analysis of Lignocellulosic Materials with 1-n-butyl-3-methylimidazolium chloride", 2007, vol. 9, pp. 63-69.
Franz et al., "Effect of Chemical Surface Heterogeneity on the Adsorption Mechanism of Dissolved Aromatics on Activated Carbon", Carbon, 2000, vol. 38, pp. 1807-1819.
Torres Galvis et al., "Supported Iron Nanoparticles as Catalysts for Sustainable Production of Lower Olefins", Science, Feb. 2012, vol. 335, No. 6070, pp. 835-838.
Gomi et al., "Purification and Characterization of Pyrocatechase from the Catechol-assimilating Yeast Candida maltosa", Agricultural and Biological Chemistry, 1988, vol. 52, No. 2, pp. 585-587.
Gurrath et al., "Palladium Cata ysts on Activated Carbon Supports Influence of Reduction Temperature, Origin of the Support and Pretreatments of the Carbon Surface", Carbon, 2000, vol. 38, pp. 1241-1255.
Harwood et al., "The β-Ketoadipate Pathway and the Biology of Self-Identity", Annual Review of Microbiology, 1996, vol. 50, pp. 553-590.
Hernández-Arranz et al., "The Translational Repressor Crc Controls the Pseudomonas putida Benzoate and Alkane Catabolic Pathways Using a Multi-tier Regulation Strategy", Environmental Microbiology, Jan. 2013, vol. 15, No. 1, pp. 227-241.

Himmel et al., "Biomass Recalcitrance: Engineering Plants and Enzymes for Biofuels", Science, Feb. 2007, vol. 315, No. 5813, pp. 804-807.
Ji et al., "Direct Catalytic Conversion of Cellulose into Ethylene Glycol Using Nickel-Promoted Tungsten Carbide Catalysts", Angewandte Chemie, Oct. 2008, vol. 120, No. 44, pp. 8638-8641.
Jiménez et al., "Genomic Analysis of the Aromatic Catabolic Pathways from Pseudomonas putida KT2440", Environmental Microbiology, Dec. 2002, vol. 4, No. 12, pp. 824-841.
Karp et al., "Alkaline Pretreatment of Corn Stover: Bench-Scale Fractionation and Stream Characterization", ACS Sustainable Chemistry Engineering, 2014, vol. 2, No. 6, pp. 1481-1491.
Korhonen et al., "Hydrophobic Nanocellulose Aerogels as Floating, Sustainable, Reusable, and Recyclable Oil Absorbent", ACS Applied Materials & Interfaces, May 2011, vol. 3, No. 6, pp. 1813-1816.
Li et al., "One Step Recovery of Succinic Acid from Fermentation Broths by Crystallization", Separation and Purification Technology, 2010, vol. 72, pp. 294-300.
Linger et al., "Lignin Valorization through Integrated Biological Funneling and Chemical Catalysis", Proceedings of the National Academy of Sciences of the United States of America, Aug. 2014, vol. 111, No. 33, pp. 12013-12018.
Luque et al., "Chemical Transformations of Succinic Acid Recovered from Fermentation Broths by a Novel Direct Vacuum Distillation-Crystallisation Method", Green Chemistry, 2009, vol. 11, pp. 193-200.
Madon et al., "Experimental Criterion for the Absence of Artifacts in the Measurement of Rates of Heterogeneous Catalytic Reactions", Industrial & Engineering Chemistry Fundamentals, 1982, vol. 21, No. 4, pp. 438-447.
Martínez et al., "Biodegradation of Lignocellulosics: Microbial, Chemical, and Enzymatic Aspects of the Fungal Attack of Lignin", International Microbiology, Sep. 2005, vol. 8, No. 3, pp. 195-204.
Marx, "Development of a Broad-host-range SacB-based Vector for Unmarked Allelic Exchange", BioMed Central Research Notes, 2008, vol. 1, pp. 1-8.
Morales et al., "The Pseudomonas putida Crc Global Regulator Controls the Expression of Genes from Several Chromosomal Catabolic Pathways for Aromatic Compounds", Journal of Bacteriology, Mar. 2004, vol. 186, No. 5, pp. 1337-1344.
Moreno et al., "The Pseudomonas putida Crc Global Regulator Controls the Hierarchical Assimilation of Amino Acids in a Complete Medium: Evidence from Proteomic and Genomic Analyses", PROTEOMICS, Jun. 2009, vol. 9, No. 11, pp. 2910-2928.
Mu et al., "Lignin Pyrolysis Components and Upgrading—Technology Review", BioEnergy Research, Dec. 2013, vol. 6, No. 4, pp. 1183-1204.
Nelson et al., "Complete Genome Sequence and Comparative Analysis of the Metabolically Versatile Pseudomonas putida KT2440", Environmental Microbiology, Dec. 2002, vol. 4, No. 12, pp. 799-808.
Niu et al., "Benzene-Free Synthesis of Adipic Acid", Biotechnology Progress, 2002, vol. 18, No. 2, pp. 201-211.
Nordlund et al., "Complete Nucleotide Sequence and Polypeptide Analysis of Multicomponent Phenol Hydroxylase from *Pseudomonas* sp. Strain CF600", Journal of Bacteriology, Dec. 1990, vol. 172, No. 12, pp. 6826-6833.
Ornston et al., "Properties of an Inducible Uptake System for β-Ketoadipate in Pseudomonas.putida", Journal of Bacteriology, Feb. 1976, vol. 125, No. 2, pp. 475-488.
Parsell et al., "Cleavage and Hydrodeoxygenation (HDO) of C-O Bonds Relevant to Lignin Conversion Using Pd/Zn Synergistic Catalysis", Chemical Science, 2013, vol. 4, pp. 806-813.
Polen et al., "Toward Biotechnological Production of Adipic Acid and Precursors from Biorenewables", Journal of Biotechnology, 2013, vol. 167, No. 2, pp. 75-84.
Prasomsri et al., "Effective Hydrodeoxygenation of Biomass-Derived Oxygenates into Unsaturated Hydrocarbons by MoO3 Using Low H2 Pressure", Energy & Environmental Science, 2013, vol. 6, pp. 1732-1738.

(56) References Cited

OTHER PUBLICATIONS

Ragauskas et al., "Lignin Valorization: Improving Lignin Processing in the Biorefinery", Science, 2014, vol. 344, No. 6185, 1246843.
Salis et al., "Automated Design of Synthetic Ribosome Binding Sites to Control Protein Expression", Nature Biotechnology, Oct. 2009, vol. 27, No. 10, pp. 946-950.
Schäfer et al., "Small Mobilizable Multi-purpose Cloning Vectors Derived from the *Escherichia coli* Plasmids pK18 and pK19: Selection of Defined Deletions in the Chromosome of Corynebacterium glutamicum", Gene, Jul. 22, 1994, vol. 145, No. 1, pp. 69-73.
Schweigert et al., "Chemical Properties of Catechols and their Molecular Modes of Toxic Action in Cells, from Microorganisms to Mammals", Environmental Microbiology, 2001, vol. 3, No. 2, pp. 81-91.
Sifontes Herrera et al., "Sugar Hydrogenation over a Ru/C Catalyst", Journal of Chemical Technology and Biotechnology, 2011, vol. 86, No. 5, pp. 658-668.
Simmons et al., "Advances in Modifying Lignin for Enhanced Biofuel Production", Current Opinion in Plant Biology, Jun. 2010, vol. 13, No. 3, pp. 312-319.
Somorjai et al., "Advancing the Frontiers in Nanocatalysis, Biointerfaces, and Renewable Energy Conversion by Innovations of Surface Techniques", Journal of the American Chemical Society, 2009, vol. 131, No. 46, pp. 16589-16605.
Sturgeon et al., "A Mechanistic Investigation of Acid-Catalyzed Cleavage of Aryl-Ether Linkages: Implications for Lignin Depolymerization in Acidic Environments", ACS Sustainable Chemistry & Engineering, 2014, vol. 2, No. 3, pp. 472-485.
Urbanus et al., "Intensified Crystallization in Complex Media: Heuristics for Crystallization of Platform Chemicals", Chemical Engineering Science, 2012, vol. 77, pp. 18-25.
van Duuren et al., "Generation of a catR Deficient Mutant of P. putida KT2440 that Produces cis, cis-Muconate from Benzoate at High Rate and Yield", Journal of Biotechnology, 2011, vol. 156, pp. 163-172.
Vardon et al., "Hydrothermal Catalytic Processing of Saturated and Unsaturated Fatty Acids to Hyrdrocarbons with Glycerol for in situ Hydrogen Production", Green Chem, 2014, vol. 16, No. 3, pp. 1507-1520.
Weber et al., "Biosynthesis of cis, cis-Muconic Acid and Its Aromatic Precursors, Catechol and Protocatechuic Acid, from Renewable Feedstocks by *Saccharomyces cerevisiae*", Applied and Environmental Microbiology, Dec. 2012, vol. 78, No. 23, pp. 8421-8430.
Wu et al., "Microbial Synthesis of cis,cis-muconic Acid from Benzoate by *Sphingobaterium* sp. GCG Generated from Effluent of a Styrne Monomer (SM) Production Plant", Enzyme Microbial Technology, Dec. 2004, vol. 35, Nos. 6-7, pp. 598-604.
Wu et al., "Microbial Synthesis of cis,cis-muconic Acid from Benzoate by *Sphingobaterium* sp. Mutants", Biochemical Engineering Journal, 2006, vol. 29, Nos. 1-2, pp. 35-40.
Yoshida et al., "Regioselective carboxylation of catechol by 3,4-dihydroxybenzoate decarboxylase of Enterobacter cloacae P", Biotechnology Letters, 2010, vol. 32, No. 5, pp. 701-705.
Yu et al., "Review of Pt-Based Bimetallic Catalysis: From Model Surfaces to Supported Catalysts", Chemical Reviews, 2012, vol. 112, No. 11, pp. 5780-5817.
Zakzeski et al., "The Catalytic Valorization of Lignin for the Production of Renewable Chemicals", Chemical Reviews, 2010, vol. 110, pp. 3552-3599.
Dunworth et al., "Investigations on the Mechanism of Catalytic Hydrogenations—XVII. Reductions with Rhodium on Activated Carbon", Journal of the American Chemical Society, 1952, pp. 1459-1462.
Muconolactone isomerase [Pseudomonas putida] GenBank BAA23629.1 Retrieved on Oct. 27, 2017. Published on Nov. 27, 1997 (Year: 1997).
Phenol monooxygenase [Plasmid pEST1226] GenBank AAC64901.1 Retrieved on Oct. 27, 2017. Published Jan. 12, 2007 (Year: 2007).
Muconate cycloisomerase [Pseudomonas putida KT2440] GenBank AAN691312.1 Retrieved on Oct. 27, 2017. Published on Mar. 5, 2010 (Year: 2010).
Protocatechuate 3,4-dioxygenase, beta subunit [Pseudomonas putida F1] GenBank ABQ80638.1 Retrieved on Oct. 27, 2017. Published Jun. 3, 2011 (Year: 2011).
Abe et al., "A Tetrahydrofolate-Dependent O-Demethylase, LigM, is Crucial for Catabolism of Vanillate and Syringate in Sphingomonas paucimobilis SYK-6", Journal of Bacteriology, Mar. 2005, vol. 187, No. 6, pp. 2030-2037.
Peters et al., Acquisition of a Deliberately Introduced Phenol Degradation Operon, pheBA, by Different Indigenous Pseudomonas Species, Applied and Environmental Microbiology, Dec. 1997, vol. 63, No. 12, pp. 4899-4906.
Daniel et al, "Biochemistry of Coenzyme $B_{12}$-dependent Glycerol and Diol Dehydratases and Organization of the Encoding Genes", FEMS Microbiology Reviews, 1999, vol. 22, pp. 553-566.
Kelada et al., "δ-Aminolevulinic Acid Dehydratase Genotype and Lead Toxicity: A HuGE Review", American Journal of Epidemiology, Jul. 1, 2001, vol. 154, No. 1, pp. 1-13.
Toraya et al, "Radical Catalysis of $B_{12}$ Enzymes: Structure, Mechanism, Inactivation, and Reactivation of Diol and Glycerol Dehydratases", CMLS Cellular and Molecular Life Sciences, 2000, vol. 57, pp. 106-127.
Anderson et al., "Occurrence, Metabolism, Metabolic Role, and Industrial Uses of Bacterial Polyhydroxyalkanoates" Microbial Reviews, Dec. 1990, vol. 54, No. 2, pp. 450-472.
Fuchs et al. "Microbial degradation of aromatic compounds—from one strategy to four", Microbiology, Nov. 2011, vol. 9, pp. 803-816.
Myung et al., "Disassembly and Reassembly of Polyhydroxyalkanoates: Recycling Through Abiotic Depolymerization and Biotic Repolymerization", Bioresource Technology, 2014, vol. 170, pp. 167-174.
Sluiter et al. "Compositional Analysis of Lignocellulosic Feedstocks. 1. Review and Desription of Methods", Journal of Agriculture and Food Chemistry, 2010, vol. 58, pp. 9043-9053.

\* cited by examiner

A

B

LIGNIN CONVERSION TO FUELS, CHEMICALS AND MATERIALS

CROSS-REFERENCE TO RELATED APPLICATIONS

This application claims the benefit of U.S Provisional Application No. 61/912,826 filed Dec. 6, 2013, the contents of which are incorporated herein by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

BACKGROUND

Lignocellulosic biomass represents a vast resource for the production of renewable transportation fuels and chemicals to offset and replace current fossil fuel usage. For many decades, worldwide research efforts have focused on the development of cost-effective processes to selectively convert the polysaccharide components of plant cell walls, namely cellulose and hemicellulose, to fuels and chemicals through biological and chemical pathways. For example, in bioethanol production, biomass typically undergoes a mild thermochemical pretreatment step followed by enzymatic hydrolysis and fermentation to produce ethanol from the monomeric components of both cellulose and hemicellulose.

The lignin component of lignocellulosic biomass is an energy-dense, heterogeneous alkyl-aromatic polymer comprised of phenylpropanoid monomers used by plants for water transport and defense, and it is the second most abundant biopolymer on Earth after cellulose. Lignin is typically underutilized in most selective conversion processes for biofuel production. In the production of fuels and chemicals from biomass, lignin is typically burned for process heat because its inherent heterogeneity and recalcitrance make it difficult to selectively upgrade the monomers to value added products. This limited ability to utilize lignin, despite being the most energy dense polymer in the plant cell wall, is primarily due to its inherent heterogeneity and recalcitrance.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide methods for producing polyhydroxyalkanoates (PHAs) from lignocellulosic biomass by treating the lignocellulosic biomass with an alkaline compound to produce an aqueous liquor, culturing the aqueous liquor with a microorganism to produce PHAs, and isolating the PHAs from the culture. Optional steps include separating the aqueous liquor from residual biomass solids (such as by filtration) before culturing, incubating the residual biomass solids with cellulase enzymes to produce sugars, and/or fermenting the sugars to biofuels by culturing the sugars with a fermentative organism.

In further embodiments, the treating of the lignocellulosic biomass with an alkaline compound is carried out in the presence of a redox catalyst such as anthraquinone.

In some embodiments, the methods also comprise a step of heating the isolated PHAs to depolymerize the PHAs to hydroxyacids and/or a step of converting the hydroxyacids to hydrocarbons by treating the hydroxyacids with a bimetallic catalyst.

In certain embodiments, the bimetallic catalyst comprises a noble metal, comprises platinum, or comprises platinum and rhenium. The bimetallic catalyst conversion step may occur in an aqueous solvent such as water.

In some embodiments, the lignocellulosic biomass is corn stover. In others, the alkaline compound is sodium hydroxide.

In various embodiments, the microorganism is a bacterium, is a bacterium from the genus *Pseudomonas*, is a species of *P. putida*, or is *P. putida* KT2440.

Additional embodiments provide integrated methods for producing hydrocarbons from lignocellulosic biomass via treating the lignocellulosic biomass with an alkaline compound to produce an aqueous liquor, separating the aqueous liquor from residual biomass solids, culturing the aqueous liquor with a microorganism to produce PHAs, isolating the PHAs from the culture, heating the isolated PHAs to depolymerize the PHAs to hydroxyacids, and converting the hydroxyacids to hydrocarbons by treating the hydroxyacids with a bimetallic catalyst. Optional steps include incubating the residual biomass solids with cellulase enzymes to produce sugars, and/or fermenting the sugars to biofuels by culturing the sugars with a fermentative organism.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

Disclosed herein are methods for the integrated production of fuels, chemicals or materials from biomass-derived lignin via aromatic catabolic pathways in bacteria. These methods enable a biological funneling approach for heterogeneous aromatic streams, thus opening a new route to produce renewable chemicals and fuels from lignin, which typically is viewed as having little value compared to the carbohydrate polymers found in terrestrial biomass. Methods to couple this biological funneling to upstream lignin depolymerization and downstream catalytic upgrading processes, thereby enabling a versatile, general approach to valorize lignin are also disclosed.

The methods presented herein may include the steps of lignin depolymerization, biological funneling to a desired intermediate, followed by recovery and transformation to a value-added product. There is significant versatility in each step of this process such that it can be adapted to various feedstocks, unit operations, and targeted fuel and chemical portfolios. Lignin may be obtained via many different routes and at various points in a biorefinery, and isolation of lignin is possible either before or after polysaccharide depolymerization as a residual solid. Depolymerization of the resulting lignin to low molecular weight aromatics can be achieved via thermal, biological, or catalytic means. In the biological funneling step, various intermediates can be targeted through genetic engineering to produce molecules from acetyl-CoA, the tricarboxylic acid cycle, and beyond in carbon metabolism. Biological funneling of lignin-derived monomers can also be combined with downstream upgrading to facilitate the development of an immense range of products.

Figure 1:
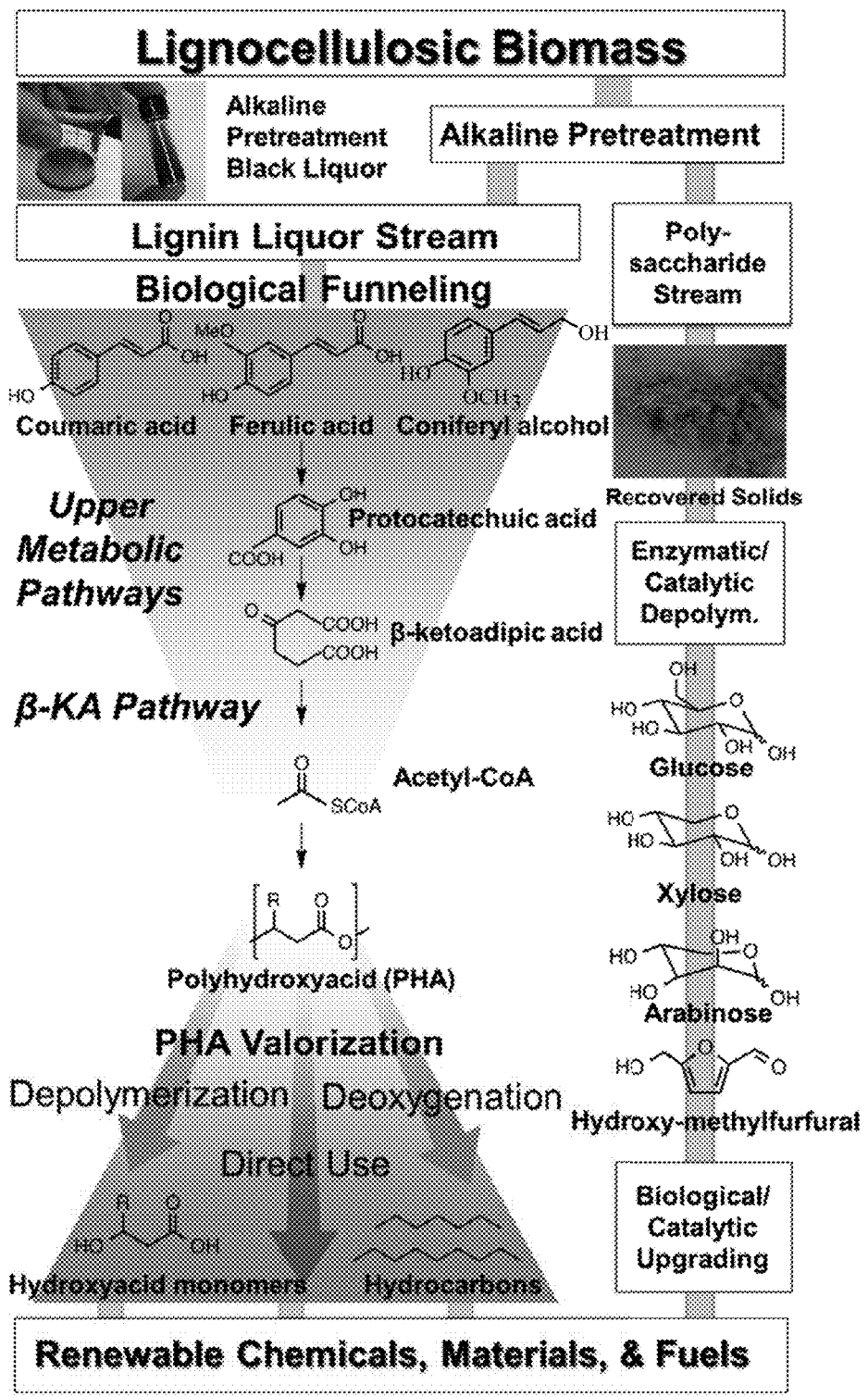
FIG. 1 shows a graphical depiction of the integrated production of fuels, chemicals, and materials from biomass-derived lignin via natural aromatic catabolic pathways.

White rot fungi and some bacteria can depolymerize lignin to its monomeric constituents using powerful oxidative enzymes. In aerobic systems, a primary mechanism employed by aromatic-catabolizing organisms involves the use of "upper pathways" in which a diverse battery of enzymes funnels aromatic monomers and oligomers to key central intermediates, such as catechol and protocatechuic acid (FIG. 1). From these central intermediates, dioxygenase enzymes oxidatively cleave carbon-carbon bonds in the aromatic rings to produce ring-opened species that are then funneled to central carbon metabolism via the β-ketoadipate pathway, ultimately leading into the tricarboxylic acid cycle. These catabolic pathways enable organisms to utilize a broad range of both natural and xenobiotic aromatic molecules as carbon and energy sources. In terms of biofuels production, these metabolic pathways offer a direct, powerful means to biologically 'funnel' the heterogeneous slate of molecules produced from lignin depolymerization into either fuels or chemicals.

As described herein, the bacterium *Pseudomonas putida* KT2440 may be used to produce medium-chain-length polyhydroxyalkanoates (mcl-PHAs) from biomass-derived lignin as part of an integrated process. The primary aromatic compounds found within lignin-derived streams are well suited for the diverse metabolic repertoire of *P. putida* for both growth and for mcl-PHA production. mcl-PHAs are high-value, biodegradable polymers that can be used as plastics or adhesives and can also be depolymerized and upgraded to chemicals or methyl-ester based fuels. mcl-PHAs are primarily generated through the fatty acid synthesis pathway when *P. putida* is grown on carbon sources metabolized through acetyl-CoA. Production is generally regulated by nutrient availability, such as a biologically accessible nitrogen source, with accumulation enhanced by nitrogen depletion.

Lignin is composed of 3 monomeric phenylpropanoid units that differ in their degree of methoxylation, which are polymerized by carbon-carbon and carbon-oxygen bonds formed during lignin biosynthesis via radical coupling reactions. The depolymerization of lignin over a broad range of catalytic, thermal, and biological routes invariably yields a chemically heterogeneous pool of products, making the production of fuels and chemicals from lignin a daunting technical challenge in biomass conversion.

The methods presented herein provide a more homogenous product group by employing aromatic catabolizing microorganisms to convert lignin components to polyhydroxyalkanoates (PHAs). These PHAs may then be thermally and catalytically converted to hydroxyacids and, in turn, to alkanes. As illustrated in FIG. 1, the heterogeneity in lignin can be overcome in a biological 'funneling' process through 'Upper Pathways' that produce central intermediates such as catechol or protocatechuic acid. Dioxygenase enzymes oxidatively cleave the aromatic rings of these central intermediates, which enter into the β-ketoadipate pathway, leading to central carbon metabolism. Lignin may thus be used for the production of medium-chain-length polyhydroxyalkanoates (mcl-PHAs), which are renewable, biodegradable plastics. mcl-PHAs may be further depolymerized to hydroxyacids, then further converted into straight-chain alkanes, thus demonstrating the concept of producing materials, chemicals, or fuels from lignin.

Lignocellulosic biomass such as corn stover may be treated with an alkaline compound to generate an aqueous lignin liquor stream. Exemplary conditions include treatment with a base such as sodium hydroxide for a time ranging from 10 minutes to several hours at a temperature ranging from about 50° C. to about 200° C. at a solids loading of 5 to 10 wt % solids in a mixer. The conditions above may be varied by one skilled in the art commensurate with the biomass source, the alkaline compound used, and other parameters.

Alkaline treatment of biomass as above typically results in a lignin-rich liquor phase and a residual solid phase rich in polysaccharides. Through this process, lignin is removed as low molecular weight species in the aqueous phase from biomass for biological upgrading. The solid phase, which mainly consists of polysaccharides, can be subjected to conversion processes to fuels or chemicals through known routes. To aid in the retention of polysaccharides in the residual solids, a redox shuttle catalyst that simultaneously oxidizes carbohydrate end groups while reductively cleaving β-O-4 linkages in lignin may be added to the alkaline treatment step. An exemplary redox shuttle catalyst is anthraquinone, which may be added at a loading of about 0.1% to 1% (wt/wt on dry biomass).

The lignin-rich liquor may be separated from the residual solids by conventional separation technologies such as filtration, centrifugation, and similar methods.

The alkaline pretreated liquor (APL) may be fed to P. putida, which upon nitrogen deprivation induces mcl-PHA production. After biological conversion of the APL, the cells may be harvested and the mcl-PHAs solvent extracted and characterized for their polymer properties. Depolymerization of the mcl-PHAS to hydroxyacids allows their use for myriad chemical applications. Subsequently, a carbon-supported bimetallic catalyst may be used to deoxygenate and reduce the resulting hydroxyacids to alkanes.

Although the methods herein are exemplified by use of the bacterium *P. putida*, any microorganism capable of biologically converting lignin-derived compounds to polyhydroxyalkoanates (PHAs) may be suitable. Exemplary microorganisms include bacteria, such as those from the genus *Pseudomonas*. Specific examples include strains of *Pseudomonas putida*, such as *P. putida* KT2440.

Conditions for microbial growth in APL are set forth in the Examples below. In general, bacteria such as *P. putida* may be grown in APL alone or APL supplemented with growth media components. Growth and PHA production rates may be modified or balanced by altering the amount of nitrogen present in the growth media. *P. putida* may be grown under nitrogen starvation conditions, or with nitrogen added into the media, either at the start of culture or during culture.

After culture, PHAs may be isolated or recovered from the culture by, for example, lysing the cells and extracting the PHAs from the lysate using a solvent such as dichloromethane. PHAs may be further purified by precipitation and solvent may be removed by drying or solvent evaporation techniques. PHAs produced from lignocellulosic biomass may be thermally depolymerized to hydroxyacids by heating or may be depolymerized by other methods known in the art.

The methods disclosed herein may include a step of converting the lignin-derived hydroxyacids to hydrocarbons by treating the hydroxyacids with a bimetallic catalyst. Suitable bimetallic catalysts include those that comprise a noble metal such as ruthenium, rhodium, palladium, silver, osmium, iridium, platinum, and gold. A secondary metal suitable for inhibiting carbon monoxide adsorption (e.g., rhenium) may also be included in the bimetallic catalyst. An exemplary bimetallic catalyst comprises platinum and rhenium metals on a carbon support. Catalyst treatment may be carried out in an aqueous solvent such as water, as described in greater detail in the Examples that follow.

Methods for breaking down the cellulose/hemicellulose components of biomass after separation of the lignin components are also disclosed herein. The separated cellulose stream may be contacted with cellulolytic or oligosaccharide degrading enzymes to result in its degradation. Treated cellulose fractions are typically degraded into simpler forms of carbohydrates, and in some cases glucose, which may then be used in the formation of ethanol or other industrial chemicals. Cellulose degradation may be achieved by culturing a microorganism in media supplemented with a source of cellulose-containing biomass or fraction thereof, in addition to media components necessary for growth of the microorganism. In addition to the use of cellulose or sugars as an energy source for the host, the growth media may need to be supplemented with additional components including, but not limited to, yeast extract.

Multiple enzymes may be needed to fully degrade the cellulose components. Such enzymes may be expressed by one or more microorganism, or purified enzymes or mixtures of enzymes may be directly added to the culture. For example, endoglucanase, exoglucanase, and β-glucosidase activities may be required to fully degrade cellulosic materials into fermentable sugars. These enzymatic activities can arise from individual enzymes, or in some cases, multiple types of cellulolytic activity can arise from the same enzyme. Further, there are different enzymatic activities that can substitute for other activities. For instance, processive endoglucanases can have overlapping roles with exoglucanases.

Exemplary enzymes with the ability to degrade carbohydrate-containing materials include cellulases with endoglucanase activity, exoglucanase activity, or β-glucosidase activity, or hemicellulases with endoxylanase activity, exoxylanase activity, or β-xylosidase activity. Additional examples include enzymes that possess cellobiohydrolase, α-glucosidase, xylanase, β-xylosidase, α-galactosidase, β-galactosidase, α-amylase, glucoamylases, arabinofuranosidase, mannanase, β-mannosidase, pectinase, acetyl xylan esterase, acetyl mannan esterase, ferulic acid esterase, coumaric acid esterase, pectin methyl esterase, laminarinase, xyloglucanase, galactanase, glucoamylase, pectate lyase, chitinase, exo-β-D-glucosaminidase, cellobiose dehydrogenase, ligninase, amylase, glucuronidase, ferulic acid esterase, pectin methyl esterase, arabinase, lipase, glucosidase or glucomannanase activities.

Fungal enzymes suitable for use in the methods disclosed herein include processive and non-processive cellulases (e.g., from GH Families 5, 6, 7, 12, 45, 74, or 9), beta-glucosidases, hemicellulases, oxidoreductases (lytic polysaccharide mono-oxygenases), and other activities. β-glucosidases are a family of exocellulase enzymes that catalyze the cleavage of β(1-4) linkages in substrates such as cellobiose, resulting in the release of glucose. In some embodiments, bacterial enzymes may also be included. Endoglucanases such as the E1 endoglucanase from *A. cellulolyticus* may also be suitable for use in the methods herein.

Suitable fungal enzymes may be derived from fungi of the genera *Trichoderma* (e.g., *T. reesei, T. viride, T. koningii,* or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A.* awamori, or *A. aculeatus*), *Fusarium*, *Neurospora*, *Hypocrea* (e.g., *H. jecorina*), and *Emericella*. In some embodiments, the fungal enzyme may be from *H. jecorina*, such as the Family 7 cellobiohydrolase Cel7A. In some embodiments, the fungal enzyme may be a commercial enzyme preparation containing one or more enzymes, such as CTec2.

Fermentative organisms such as yeasts and bacteria may be used to ferment simple sugars (such as those resulting from cellulose degradation) directly to biofuels. The organisms are contacted with the sugars in a fermentation broth under conditions suitable for fermenting the sugars to biofuels. Fermentation conditions vary with the organism, feedstock or sugar used, or with the desired biofuel product, and can be determined by those skilled in the art.

The resulting products after cellulose degradation and fermentation may be isolated or purified. After fermentation, for example, a biofuel may be separated from the fermentation broth by any conventional technique known to separate alcohol from aqueous solutions, including evaporation, distillation, solvent extraction and membrane separation. Solids such as microorganisms may be removed before separation to enhance separation efficiency. Fermentation products may also be converted to products other than ethanol. Examples include conversion to higher alcohols, hydrocarbons, or other advanced fuels via biological or chemical pathways, or combination thereof.

Lignocellulose-containing biomass may be derived from any source known in the art, and may be degraded to oligosaccharides and simple sugars using enzymes or chemicals. Biofuels such as ethanol may be subsequently produced from the fermentation of sugars derived from the cellulosic materials. Examples include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure. Biomass samples may be milled, processed or pretreated using known methods prior to use in the methods herein.

EXAMPLES

Example 1

Corn Stover Pretreatment

To obtain a lignin-rich stream for upgrading, 100 kg of ¼" hammer milled corn stover was pretreated with sodium hydroxide at a loading of 70 mg NaOH/g dry stover and a 0.2% charge of anthraquinone (AQ; w/w on dry stover) at 7 wt % solids in a 1,900 L, jacketed paddle mixer (American Process Systems, Gurnee, Ill.). The slurry was heated to 100° C. indirectly by applying 30-40 psig of saturated steam on the vessel jackets. The heat ramp was approximately 2 hours. After 30 minutes at temperature, the slurry was cooled to 60° C. by cycling cooling water at 15-20° C. through the jackets, and the warm alkaline pretreated liquor (APL) was gravity drained from the solid, collected in drums, and stored in a cold room at 4° C. The APL pH was approximately 12. A continuous screw press (Vincent Corp. Model CP10, Tampa, Fla.) was subsequently used to dewater the pretreated stover to approximately 20 wt % total solids. APL recovered by pressing was added to the gravity-drained liquor collected immediately after pretreatment. The APL is highly enriched in lignin-derived compounds. Anthraquinone acts as a redox shuttle catalyst that simultaneously oxidizes carbohydrate end groups while reductively cleaving β-O-4 linkages in lignin. This increases the retention of polysaccharides in the solid phase, since the oxidized carbohydrate end groups are resistant to solubilization via peeling reactions, and creates more low molecular weight lignin fragments in the liquor phase through the increased cleavage of β-O-4 bonds.

Example 2

Compositional Analysis of Pretreated Solids

Compositional analysis was conducted on the pretreated residual solids to quantify the carbohydrate retention and lignin removal. The mass of the recovered dry solids was measured by drying a subsample of solid fraction for several days in a 40° C. vacuum oven until the mass stabilized to a constant value. Compositional analysis of the recovered solids was subsequently performed in accordance with standard published procedures (Sluiter et al., *J Agr Food Chem* 2010, 58:9043). The alkaline pretreated liquor (APL) is a heterogeneous mixture of acids, polysaccharides, monosaccharides, aromatic monomers (derived from lignin), high molecular weight lignin, and acetate. The complexity of black liquor and its sensitivity to pH changes complicates direct, detailed compositional analysis. Therefore, the composition of the APL is reported by difference from the known mass and composition of the dry biomass loaded into the pretreatment vessel and the resulting mass and composition of the retained solids, as shown in FIG. 4.

Figure 4:
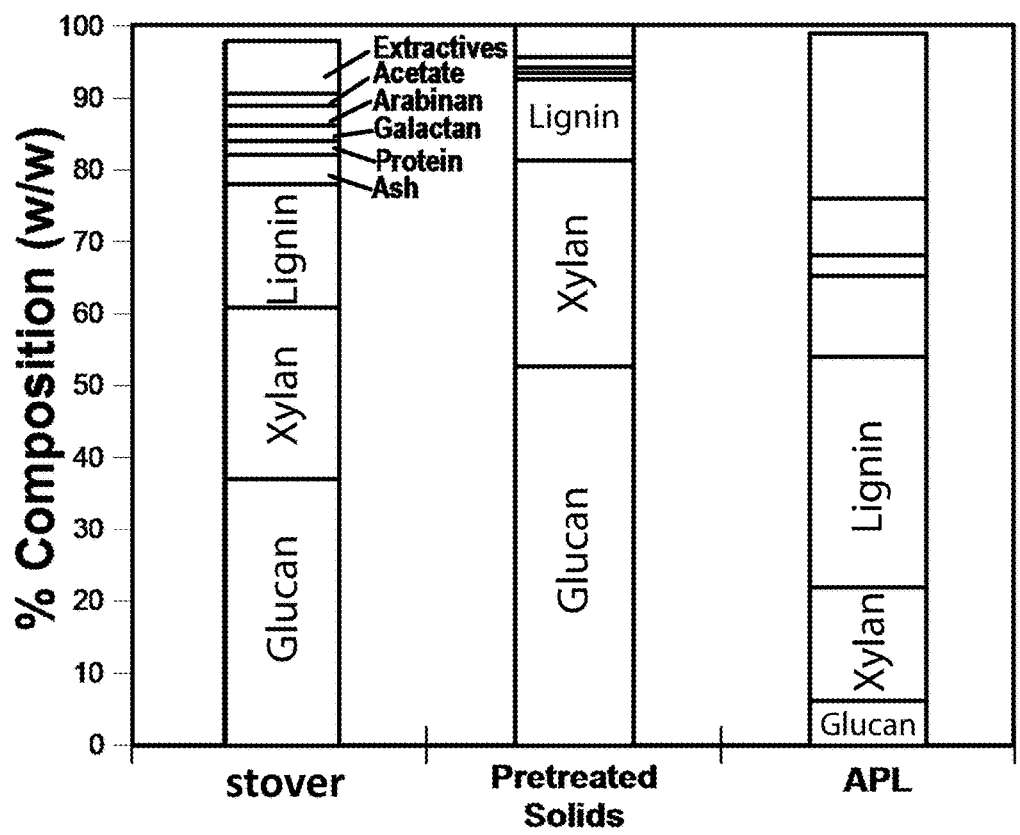
FIG. 4 shows compositional analyses for untreated corn stover and biomass subjected to alkaline treatment.

FIG. 4 shows the composition of the starting corn stover, resulting pretreated solids, and the composition of the material solubilized into the APL on a w/w basis. The pretreatment conditions for the material shown here are 100° C. for 30 minutes with a NaOH loading of 70 mg NaOH/g dry stover at 7 wt % solids and 0.2% AQ charge (w/w on dry corn stover). The initial corn stover is shown in the left most bar and has a w/w composition of: 37% glucan, 24% xylan, 17% lignin, 4% ash, 2% protein, 2% galactan, 3% arabinan, 2% acetate, and 7% extractives. The recovered solids are enriched in carbohydrates and retain only 67% of the mass of the dry corn stover loaded into the reactor. The measured w/w composition of the pretreated solid, shown in the middle bar, is: 53% glucan, 29% xylan, 11% lignin, 1% ash, 1% protein, 1% galactan, 5% arabinan, 0% acetate, and 0% extractives. The composition of the material solubilized into the APL is presented in the right most bar labeled "APL" and its w/w composition is: 6% glucan, 16% xylan, 32% lignin, 11% ash, 3% protein, 0% galactan, 0% arabinan, 8% acetate, and 23% extractives.

Figure 5:
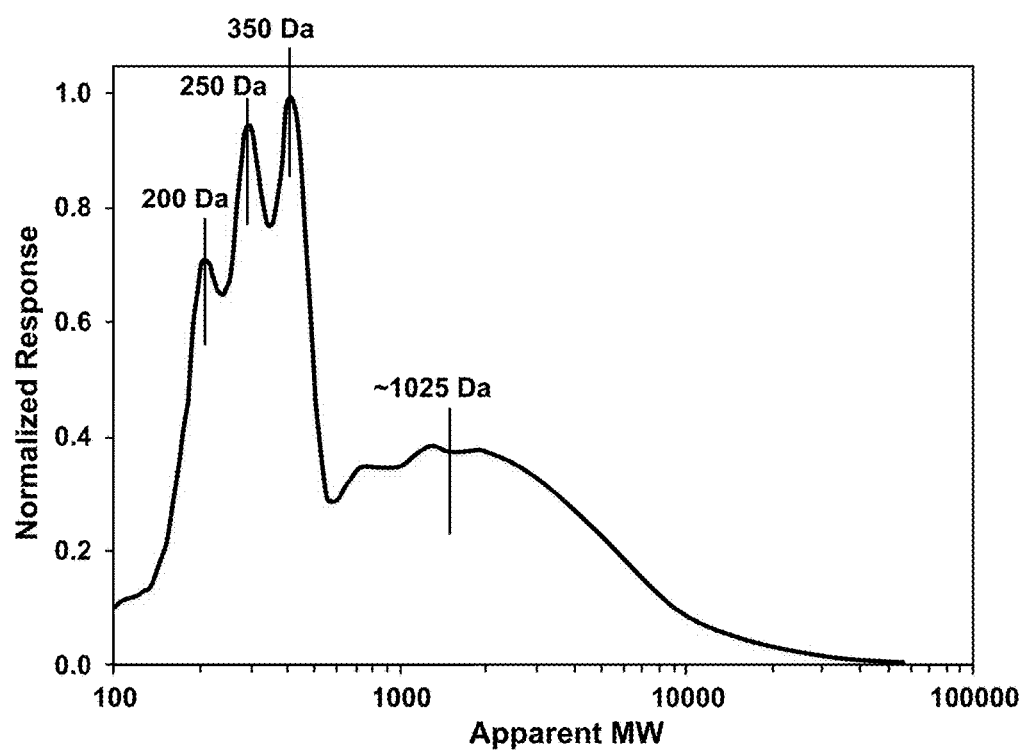
FIG. 5 the molecular weight distribution of alkaline pretreated liquor obtained by gel permeation chromatography analysis.
Figure 6:
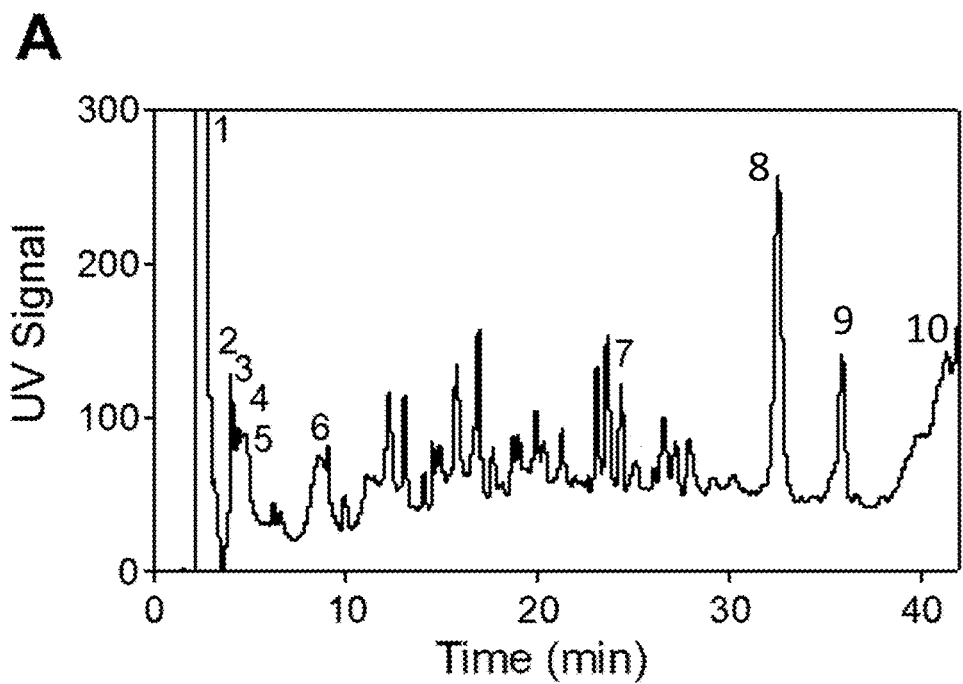
FIG. 6 shows (A) the chromatogram obtained from alkaline pretreated liquor using liquid chromatography, for retention times between 0 and 42 minutes and (B) the chromatogram from alkaline pretreated liquor for retention times between 40 and 60 minutes, the y axis scale for these retention times has been expanded from that presented in (A) to capture the full peak heights in this region.
Figure 6:
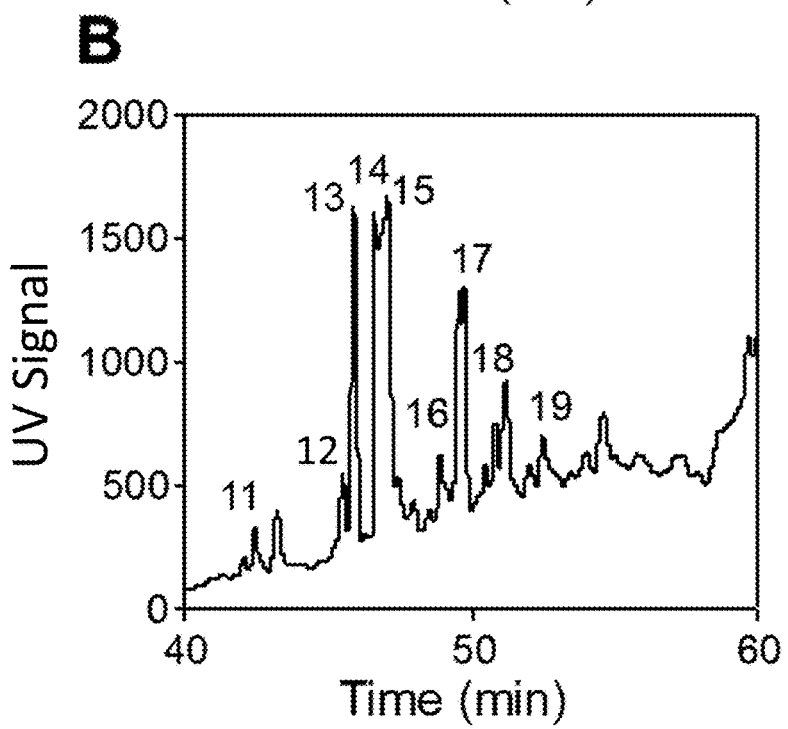
Figure 7:
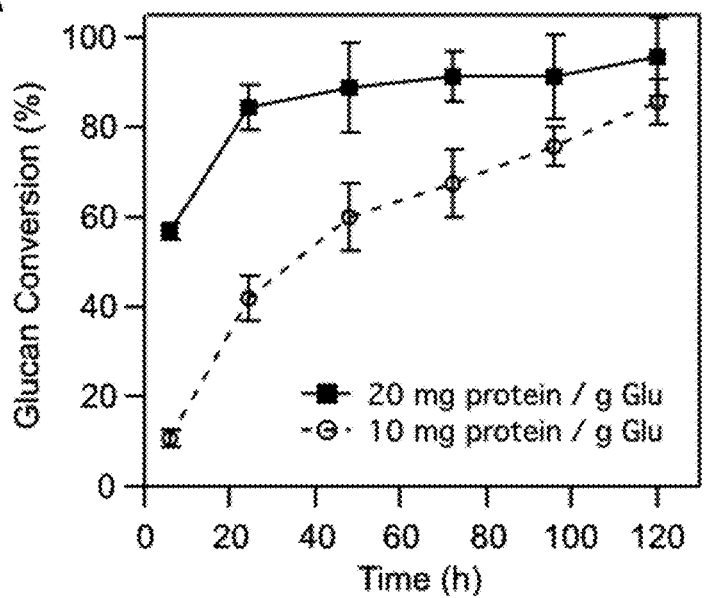
FIG. 7 shows the results of enzymatic hydrolysis of residual solids after alkaline pretreatment. (A) Glucan (cellulose) conversion at 20 mg enzyme/g glucan and 10 mg enzyme/g glucan. (B) Xylan conversion at 20 mg enzyme/g glucan and 10 mg enzyme/g glucan. Digestions were conducted at 1 wt % solids loading at 50° C., pH=5.0.
Figure 7:
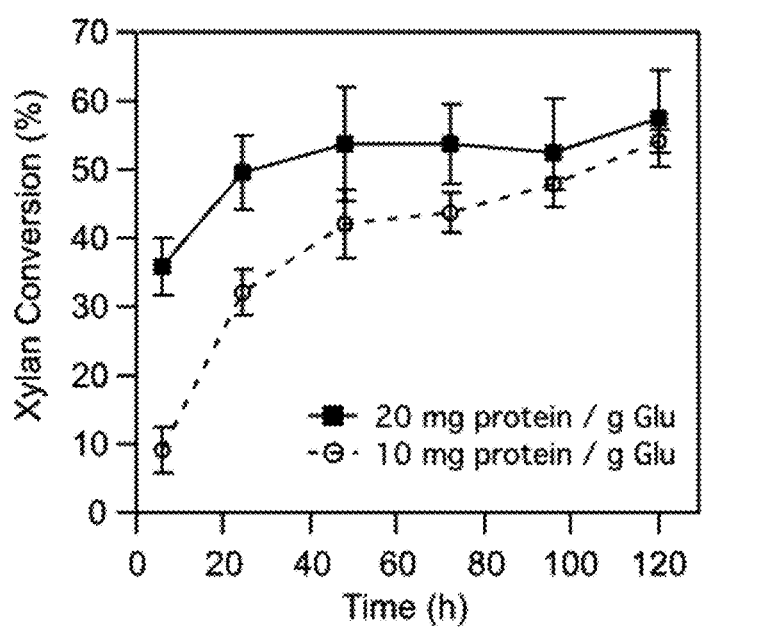

From alkaline pretreatment, 56% of the lignin in biomass is fractionated to the APL while 95% of the glucan and 81% of the xylan are retained in the solids. The material solubilized to the APL consists mostly of lignin, small molecule extractives, inorganic components, and acetate, at 32%, 23%, 11% and 8% w/w, respectively (FIG. 4). As shown in FIG. 5, the APL molecular weight distribution consists of major species at 200, 250, and 350 Da, suggesting the majority of the APL components are monomers, dimers, and trimers. Major components include p-coumaric acid, vanillic acid, ferulic acid, acetate, and syringealdehyde among many others (Table 1, FIG. 6). Additionally, the residual solids, which are enriched in polysaccharides, are readily digestible by an industrial cellulase cocktail, easily reaching high conversion of both glucan and xylan within 48 hours (FIG. 7).

Example 3

Gel Permeation Chromatography (GPC) Analysis

To determine the molecular weight distribution of the alkaline pretreated liquor (APL), 20 mg of APL obtained from the alkaline pretreatment of corn stover (described in Example 1 above) was acetylated in a mixture of pyridine (0.5 mL) and acetic anhydride (0.5 mL) at 40° C. for 24 hours with stirring. The reaction was terminated by addition of methanol (0.2 mL) to neutralize the acetic anhydride. The acetylation solvents were then evaporated from the samples at 40° C. under a stream of nitrogen gas. The samples were further dried in a vacuum oven at 40° C. overnight. A final drying was performed under vacuum (1 torr) at room temperature for 1 hour. The dried acetylated samples were dissolved in tetrahydrofuran (THF, Baker HPLC grade) and then filtered (0.45 μm nylon membrane syringe filters) before GPC analysis. The acetylated samples appeared to be completely soluble in THF. GPC analysis was performed using an Agilent HPLC with 3 GPC columns (Polymer Laboratories, 300×7.5 mm) packed with polystyrene-divinyl benzene copolymer gel (10 μm beads) having nominal pore diameters of $10^4$, $10^3$, and $10^2$ Å. The eluent was THF and the flow rate was 1.0 mL/min. An injection volume of 25 μL was used. The HPLC was attached to a diode array detector measuring absorbance at 260 nm (band width 40 nm). Retention time was converted into molecular weight (MW) by applying a calibration curve established using polystyrene standards.

As depicted in FIG. 5, the APL shows three large peaks of low molecular weight components at apparent molecular weights of about 200, 250, and 350 Da, suggesting the majority of the components in the APL are in the monomer, dimer, and trimer range. A broad peak centered at an apparent molecular weight of about 1,025 Da may represent lignin fragments that are not fully depolymerized. The overall apparent molecular weight average of the APL is 1,100 Da. The larger intensity of the low molecular weight components points to the effectiveness of the anthraquinone additive, which increases the fragmentation of the lignin polymer during pretreatment.

Example 4

Liquid Chromatography Identification of Liquor Components

Liquid chromatography was employed to identify the primary components in alkaline pretreated liquor (APL). Individual chemical standards representing the compounds denoted in Table 1 without asterisks were purchased from Sigma-Aldrich, St. Louis, Mo., with the exception of acetic acid (Fisher Scientific, Pittsburgh, Pa.). HPLC solvents and modifiers consisted of deionized water (DI; Barnstead Easy Pure$^{II}$, Waltham, Mass.), acetonitrile (Fisher HPLC grade), and formic acid (Sigma-Aldrich).

Analysis of samples was performed on an Agilent 1100 LC equipped with a G1315B Diode Array Detector (DAD) and in-line Electrospray Ionization (ESI) 2440A Mass Selective Detector (MSD) Ion Trap SL (Agilent Technologies, Palo Alto, Calif.). Each sample was placed in a cooled auto-sampler (10° C.) and injected at a volume of 50 μL into the LC/MS system. Sample compounds were separated using reverse-phase chromatography on an YMC C30 Carotenoid 0.3 μm, 4.6×150 mm column (YMC America, Allentown, Pa.). The LC/MS method consisted of eluent gradients, flow rates, temperatures, and configurations according to established methods. The degassed solvent regime consisted of eluent A) DI modified with 0.03% formic acid, and eluent B) 9:1 acetonitrile and DI water also modified with 0.03% formic acid, which was prepared fresh at least 4 hours prior to analyses in order to stabilize.

Flow from the HPLC DAD was directly routed to the ESI-MSD Ion Trap. Tandem MS of major contributing ions was carried out via direct infusion on an Agilent 2440A MSD Ion Trap SL equipped with ESI source operating in negative mode. Source and Ion Trap conditions were calibrated and optimized with Agilent ESI-T tuning mix (P/N: G2431A) and using smart parameter setting (SPS) tuning with target m/z set to 165, compound stability 70%, trap drive 50%, capillary at 3500 V, fragmentation amplitude of 0.8 V with a 30 to 200% ramped voltage implemented for 50 ms, and an isolation width of 2 m/z (He collision gas). The ESI nebulizer gas was set to 60 psi, with dry gas flow of 11 L/min held at 350° C. A MS scan and precursor isolation-fragmentation scans were performed across the range m/z: 40-350.

Table 1 presents low molecular weight components of alkaline pretreatment liquor identified from the liquid chromatography analyses with their respective retention times (RT). Also listed, are commonly identified monomers in pulping liquors reported in previous literature (compounds marked with an asterisk).

TABLE 1

| Peak No. | RT (min) | Catalytic Deoxygenation Species |
|---|---|---|
| 1 | 2.3 | Malonic acid |
| 2 | 2.7 | Malic acid |
| 3 | 2.8 | Acetic acid |
| 4 | 2.9 | Lactic acid |
| 5 | 4.9 | Citric acid |
| 6 | 9.4 | Levulinic acid |
| 7 | 25.2 | Salicylic acid |
| 8 | 32.5 | 4-Hydroxybenzaldehyde |
| 9 | 35.6 | Vanillic acid |
| 10 | 42.5 | Syringic acid |
| 11 | 43.3 | Vanillin |
| 12 | 46.4 | Syringealdehyde |
| 13 | 46.6 | p-Coumaric acid |
| 14 | 49.0 | Ferulic acid |
| 15 | 49.9 | Sinapic acid |
| 16 | — | Coniferyl alcohol* |
| 17 | — | Coniferyl aldehyde* |
| 18 | — | Eugenol* |
| 19 | — | Guaiacol* |
| 20 | — | Sinapyl alcohol* |
| 21 | — | Syringol* |
| 22 | — | Vanillyl Alcohol* |

*Known from previously literature

An internal spectral database consisting of compounds previously identified as degradation products was developed based on ESI-MS-MS scans for the precursor (M-H)$^-$ ion and product ion of each compound (Table 1, compounds marked with an asterisk) through direct infusion experiments, as described in the literature. Both the database search results for total ion chromatography and extracted ion chromatography for the precursor (M-H)$^-$ ion were used to confirm the identity of compounds, while deconvolution of mass/charge ion fragmentation patterns was utilized to predict the identity of unknown compounds observed within the samples. The concentrations of identified analytes were determined based on 6-point linear concentration-area response curves as recorded by the DAD at 210 nm (0.001 to 0.1 g/L prepared mixes) and forced through a zero intercept.

The resulting concentration-response curves exhibited linear correlation coefficients greater than $R^2=0.97$ (Table 1), and with this agreement any observed responses outside these levels was projected assuming linearity. Additional standard mix concentrations up to 1 g/L were analyzed, however UV responses for levels above 0.1 g/L became unstable for several compounds, which resulted in a shift to a slight polynomial-fit across the full concentration range. The linear dynamic range maximum for each compound marked this point of instability, where correlation coefficients for linear regression started to fall below 0.95. The observed decrease in area response relative to concentration at these higher levels (>0.1 g/L) for many compounds was attributed to a consequence of UV response degradation approaching detector saturation and widening of peaks to the point of unresolved baseline and peak separations. The observed linear maximum levels were all in agreement or surpassed those reported in the literature. Limits of detection observed in this work were also in agreement with prior reports. A mixed standard containing these same compounds at 0.025 mg/mL was used as a check standard and to evaluate instrument response before and after analysis of sample unknowns.

FIG. 6A shows the chromatogram obtained from APL using the liquid chromatography method described above, for retention times between 0 and 42 minutes. FIG. 6B shows the chromatogram from APL for retention times between 40 and 60 minutes. The y axis scale for these retention times has been expanded from that presented in (A) to capture the full peak heights in this region.

Example 5

Enzymatic Hydrolysis

Enzymatic hydrolysis of the residual solids was conducted to determine the digestibility. Alkaline pretreated corn stover solids were washed five times with deionized water and stored in 30 mM NaAc, pH 5.0, and at 4° C. prior to enzymatic hydrolysis. Fungal cellulase enzymes (CTec2, Novozymes) were loaded at 10 or 20 mg of protein per g of glucan in a 1% biomass solids slurry and incubated at 50° C. in 20 mM NaAc, pH 5.0, for 120 hours. Digestions were conducted in sealed 1.5-mL vials with continuous mixing by inversion at 10-12/min. Substrates were loaded at 10 mg dry biomass per mL in 1.4 mL reaction volumes. Representative (with respect to both solid and liquid phases of the digestion slurry) 0.1-mL samples were withdrawn from well-mixed digestion slurries at selected time-points during the digestions. The aliquots were then diluted 10-fold with deionized water and immersed in a boiling-water bath for 10 minutes to inactivate the enzymes and terminate the reaction. The diluted and terminated digestion aliquots were then filtered through 0.2-µm nominal-pore-size nylon syringe-filters (Pall/Gelman Acrodisc-13) to remove residual substrate and most of the denatured enzyme.

Released cellobiose and glucose and xylose in the diluted samples were then determined by HPLC analysis on an Aminex HPX-87H column (Bio-Rad Laboratories, Inc., Hercules, Calif., USA) operated at 55° C. with 0.01 N $H_2SO_4$ as mobile phase at 0.6 mL/min in an Agilent 1100 HPLC system with refractive-index detection. The resulting glucose, cellobiose, and xylose concentrations calculated (in mg/mL) for each digestion mixture was converted to anhydro-glucose and anhydro-cellobiose concentrations, respectively, by subtracting out the proportional weight added to each molecule by the water of hydrolysis. The sum of the concentrations of anhydro-glucose and anhydro-cellobiose, which sum is equivalent to the weight-concentration of the glucan chain that was hydrolyzed to produce the soluble sugars, was then divided by the initial weight-concentration of glucan and xylan in the digestion mixture and multiplied by 100% to yield activity results as percent conversion. FIG. 7 shows glucan (cellulose) conversion at 20 mg enzyme/g glucan and 10 mg enzyme/g glucan (A) and xylan conversion at 20 mg enzyme/g glucan and 10 mg enzyme/g glucan (B). Digestions were conducted at 1 wt % solids loading at 50° C., pH 5.0.

Example 6

Preparation of APL for *P. putida* Growth

As described above, the APL was produced at a pH of about 12. For growth of *P. putida*, the APL was slowly titrated to pH 7.0 using 10 N $H_2SO_4$. Following neutralization of the APL, a 10% volume of 10× modified M9 salts (Per liter of 10×M9: 6.78 g $Na_2PO_4$, 3 g $KH_2PO_4$, 0.5 g NaCl, 10 N NaOH to pH 7.0, and no supplemented carbon source), was supplemented to the APL. Following mixing, 2 mL of 1 M $MgSO_4$ and, 100 µL 1 M $CaCl_2$ were added to the M9-APL. It was noted that *P. putida* was also able to grow in unsupplemented APL with a reduced growth rate.

Example 7

Fermentations

Figure 2:
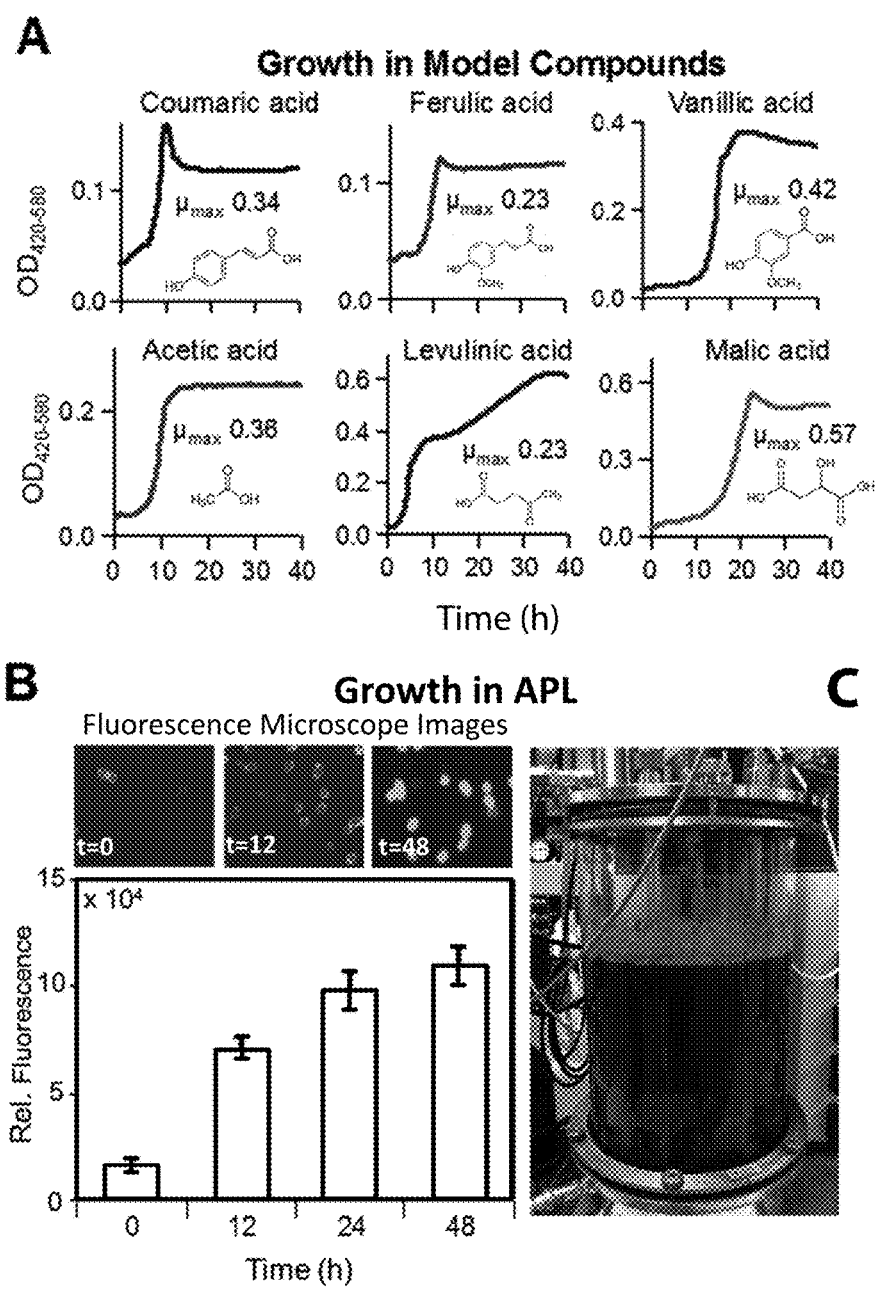
FIG. 2 illustrates the biological conversion of lignin-derived aromatic molecules to mcl-PHAs. (A) Growth curves and maximum growth rates (μmax) of *P. putida* on representative model compounds present in APL demonstrate that the particular APL components are metabolized during biological conversion of APL. (B) Fluorescence imaging of *P. putida* at 0, 12, and 48 hours stained with Nile Red demonstrates mcl-PHA production from APL. Fluorescence quantitation of *P. putida* cells from the APL conversion as a function of time adjusted to an equivalent cell density. (C) Biological conversion of APL by *P. putida* in a 14 L fermentation vessel.

To produce mcl-PHAs from APL, *P. putida* was grown in neutralized APL in the absence of an external nitrogen source (FIG. 2). Given the complexity of the APL, we first screened *P. putida* growth on several individual compounds present in APL (FIG. 2A). As shown, *P. putida* consumes many of these species, highlighting the fact that the organism is well suited to the complexity of APL, concomitant with its metabolic diversity. Following growth on APL in a 14-L fermentor (FIG. 2C), cells were recovered via centrifugation and lyophilized for mcl-PHA recovery.

Overnight cultures of *P. putida* were grown in LB medium and typically reached an Optical Density at 600 nm ($OD_{600}$) of 3.5 to 4.0. These seed cultures were centrifuged and washed once in 1×M9 medium and used to inoculate cultures to a starting $OD_{600}$ of 0.05 in M9-APL (described above). Supplemental nitrogen $(NH_4)_2SO_4$ was either withheld altogether, or added to 1 mM to optimize the balance between biomass formation and PHA production as a function of nitrogen starvation. All growths were conducted at 30° C. For fermentations, we used 14 L BioFlo 3000 reactors (New Brunswick Scientific, CT). Reactors were held constant at 30° C., and constant mixing was achieved using double impellers (marine impeller at bottom, Rushton impeller at mid-culture height) at 200 rpm. Aeration was set at 0.35 VVM using 100% air and pH was controlled at pH 7.0 using KOH/HCl. Fermentations were allowed to run for 72 hours followed by centrifugation to harvest cells for mcl-PHA extraction.

Example 8

Growth Curves

To examine the ability of *P. putida* to utilize substrates found in APL, M9 medium supplemented with various carbon sources was used and growth analysis was performed using an $OD_{420-580}$-based and a Bioscreen C instrument (Growth Curves USA, Piscataway N.J.). Individual carbon sources were dissolved in $H_2O$ at 4 g/L to create a 2× solution. In some cases, 4 g/L exceeded the solubility of the compounds at 30° C. in 1 hour, so residual solid was removed during filter sterilization. Growths were performed in triplicate in a final volume of 300 µL. To generate the final media, 120 µL of concentrated M9-salts (no supplemented carbon, and 10 mM $(NH_4)_2SO_4$) was added to each well such that the final M9 concentration of the 300 µL cultures was 1×. 150 µL of each 2× carbon source was then added to each well such that each carbon source was at 2 g/L (or below in the cases that 2 g/L exceeded the max solubility of the compound). Overnight cultures of P. putida KT2440 were grown in M9-glucose, washed in M9- and suspended in M9- to an $OD_{600}$ of 0.3. Thirty microliters of this culture was then added to each well to establish an initial $OD_{420-580}$ of 0.03. Absorbance readings were taken every 15 minutes for 42 hours. Growth curves were plotted and the maximum growth rate (µmax) was defined as the maximum slope of the growth curve over any 4 hour period during the experiment. Each growth was performed in triplicate, and these were averaged to calculate µmax. One representative curve was selected for the specific compounds shown in FIG. 2.

Example 9

Flow Cytometry of Polyhydroxyalkanoate Accumulation

To monitor mcl-PHA accumulation during the fermentations, Nile Red staining and detection using a FACS Aria fluorescence activated cell sorter (BD Biosciences, San Jose Calif.) was used. One mL of cell culture was centrifuged and washed in phosphate buffered saline (PBS). Cells were then stained using 0.5 mg/ml Nile Red dissolved in DMSO for 15 minutes, then washed twice in PBS. Samples were loaded into the FACSAria and screened for Nile Red Fluorescence using a 488 nm wavelength laser coupled with 610/20 nm detection with the peak intensity of each event recorded. For each sample 20,000 events were recorded to generate the histograms.

Figure 8:
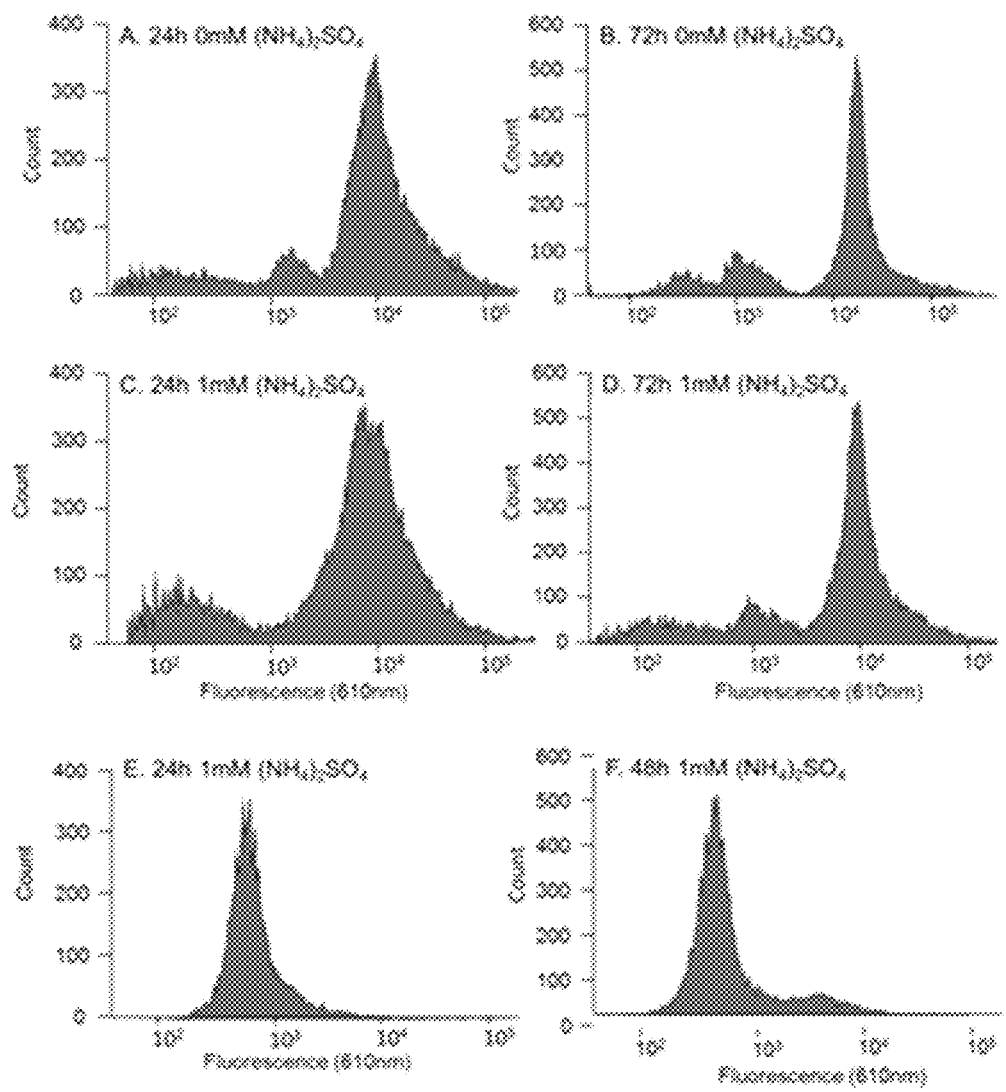
FIG. 8 shows flow cytometry histograms of Nile Red stained cells to monitor mcl-PHA production in *P. putida* grown in APL or APL supplemented with 1 mM $(NH_4)_2SO_4$ during 10 L fermentations.

FIG. 8 shows histograms of Nile Red stained cells to monitor mcl-PHA production in P. putida grown in APL (A, B) or APL supplemented with 1 mM $(NH_4)_2SO_4$ (C, D) during 10 L-cultivations. Additionally, a culture grown in APL supplemented with 10 mM $(NH_4)_2SO_4$ (50 mL in 250 mL baffled flasks) is shown to highlight the nitrogen-limitation dependence of PHA production in APL over 48 hours (E, F). Flow cytometry results shown in FIG. 8 demonstrate that most of the cell population produces mcl-PHAs.

Example 10

Fluorescence Microscopy and Quantitation

The ability of P. putida to produce mcl-PHAs when grown in APL as a sole carbon source was examined. FIG. 2B demonstrates intracellular mcl-PHA accumulation over 48 hours as shown by Nile Red staining. Fluorescence intensity is shown to increase over time in individual cells via fluorescent quantitation and imaging. The primary increase in fluorescence, and thus likely in mcl-PHA production, occurs in the first 24 hours of cultivation, similar to mcl-PHA growth observed on carbohydrates and other homogeneous substrates in other P. putida strains.

PHA accumulation was visually assayed using epifluorescence microscopy. To prepare cells for imaging, 1 mL of culture grown in APL was harvested at 0, 6, 12, 24, and 48 hours post-inoculation via centrifugation at 5,000×g at room temperature for 5 minutes. The culture supernatant was removed, and cells were washed twice in 1×PBS, fixed in 3:1 ethanol:acetic acid for 10 minutes, and washed twice in 1×PBS, followed by resuspension in 1 mL 1×PBS. Cells were stained with 10 µg/mL Nile Red (Molecular Probes, Invitrogen Corporation) for 5 minutes, and immobilized on microscope coverslips by mixing with 1% low-melting-temperature agarose (heated to 65° C. to solubilize) in a 1:1 ratio. Images were acquired using a Nikon Eclipse 80i microscope. Nile Red fluorescence was detected between 560 and 590 nm using band-pass filtering.

Fluorescence emission of Nile Red was obtained using a FLUOstar Omega microplate reader (BMG Labtech, Cary, N.C.), equipped with emission and excitation filters of 485/12 and 590/10 nm, respectively. Cells were harvested, diluted to $OD_{600}$=0.1 in M9 media, washed in 1×PBS, and stained with Nile Red, as described above. Top optic positioning was utilized with 0.2 s positioning delay, a gain setting of 500, and 10 flashes per well. All measurements were obtained in 96-well, black, round-bottom plates (Corning Costar) at room temperature, in 200 µL reaction volumes.

Example 11

Polyhydroxyalkanoate Recovery and Characterization

Figure 3:
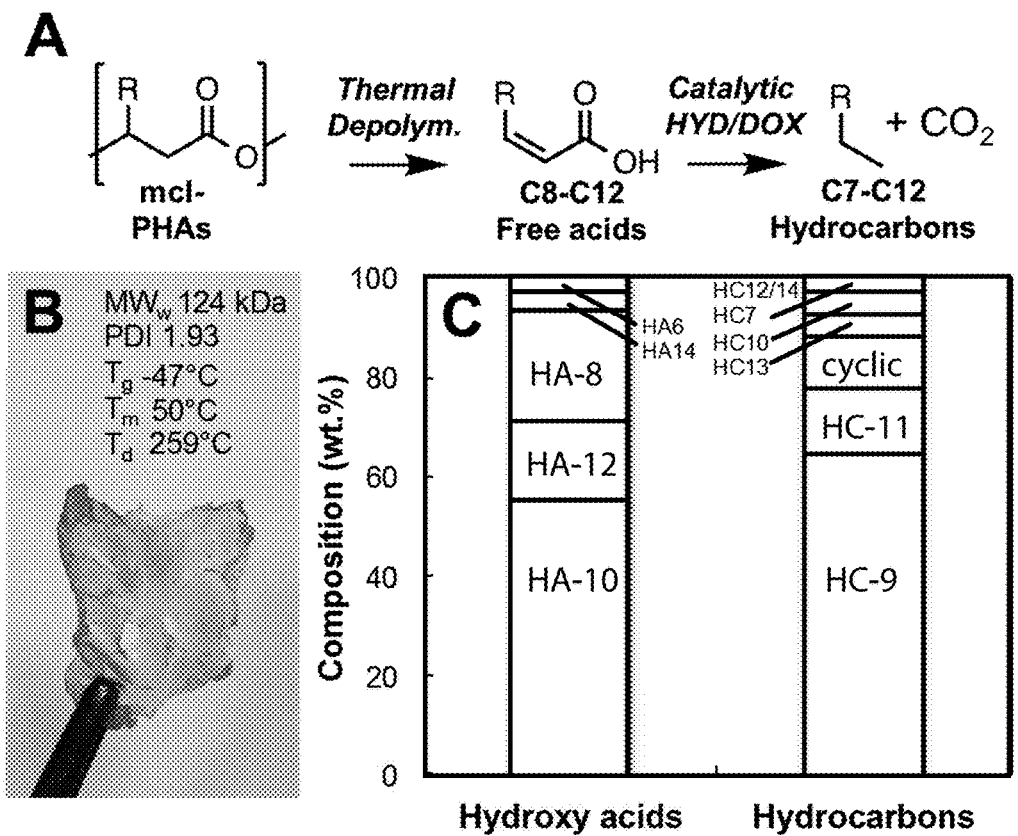
FIG. 3 shows lignin-derived mcl-PHA physicochemical properties and catalytic upgrading to chemical precursors and fuels. (A) Example thermal-catalytic upgrading pathway for mcl-PHAs to chemical precursors and hydrocarbon fuels. (B) Lignin-derived mcl-PHAs and physicochemical properties including weight-average molecular weight (MWw), polydispersity index (PDI), glass transition temperature (Tg), melting point (Tm), and 5% decomposition temperature (Td). (C) Initial mcl-PHA hydroxyacid composition (left) and alkane distribution (right) after thermal depolymerization and catalytic deoxygenation.
Figure 9:
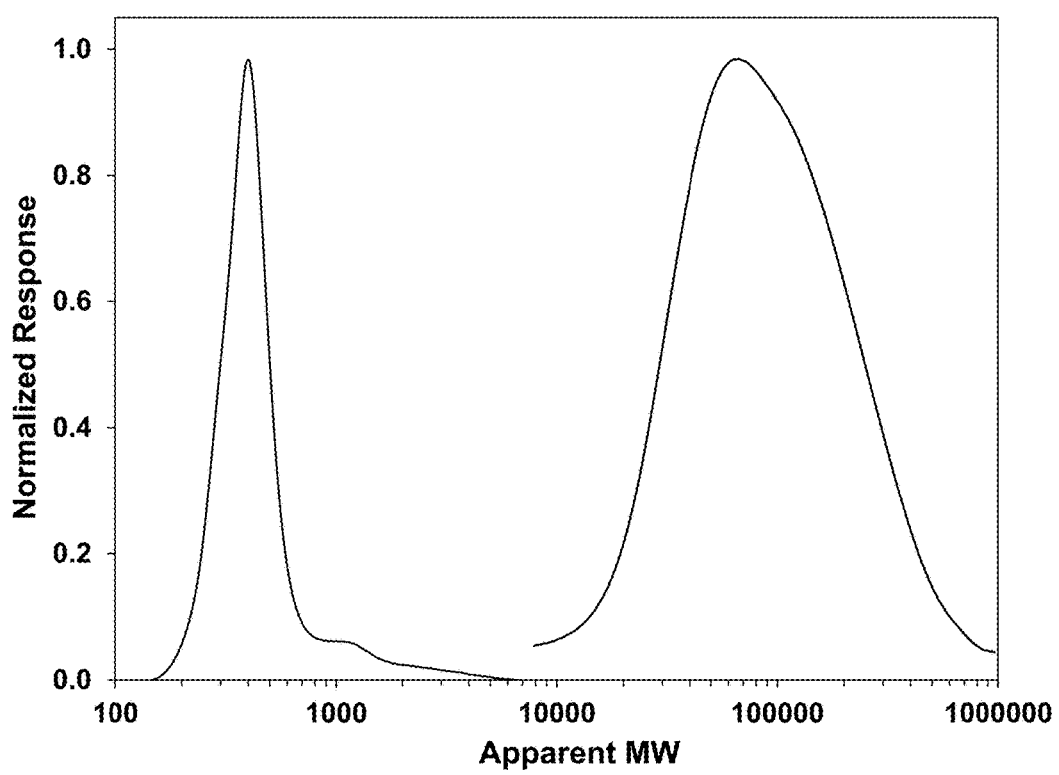
FIG. 9 shows a gel permeation chromatogram of mcl-PHAs.
Figure 10:
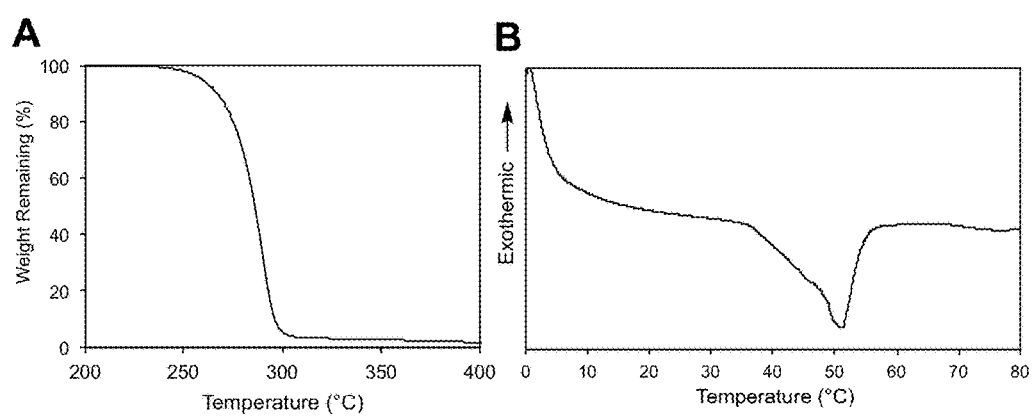
FIG. 10 shows the results of thermal decomposition and differential scanning calorimetry of mcl-PHAs.

PHAs derived from lignin were evaluated to determine their properties and to demonstrate the conversion to chemical precursors and fuels (FIG. 3A). In terms of material properties, mcl-PHA monomer distribution and oligomer chain length can be tailored for desired polymer characteristics depending on the intended application. APL-derived mcl-PHAs shown in FIG. 3B recovered from P. putida displayed a weight average MW (MWw) of 124 kDa (FIG. 9), polydispersity index (PDI) of 1.93, and a glass transition, melting, and decomposition temperatures of –49° C., 65° C., and 259° C., respectively (FIGS. 3B and 10). Analysis of the hydroxyacid monomer distribution showed that the mcl-PHA polymer was comprised primarily of 3-hydroxydecanoic acid (55%), 3-hydroxydodecanoic acid (22%), 3-hydroxyoctanoic acid (16%), 3-hydroxytetradecancoic acid (4%), and 3-hydroxyhexanoic acid (3%) (FIG. 3C, left panel).

Polyhydroxyalkanoates (PHAs) were extracted with dichloromethane from P. putida recovered from APL using a Dionex 200 Accelerated Solvent Extractor (ASE). The extraction was performed at 50° C. and 10 MPa over 4 cycles with a 100% flush volume. The dichloromethane extract was concentrated to 10% of the initial volume using a rotary evaporator, and the PHAs were precipitated from the crude extract using ice-cold ethanol. Residual solvent was removed under flowing $N_2$ at 40° C., prior to drying under vacuum at 40° C. overnight to determine the purified PHA yield.

Example 12

Polyhydroxyalkanoate Thermal Depolymerization

Figure 11:
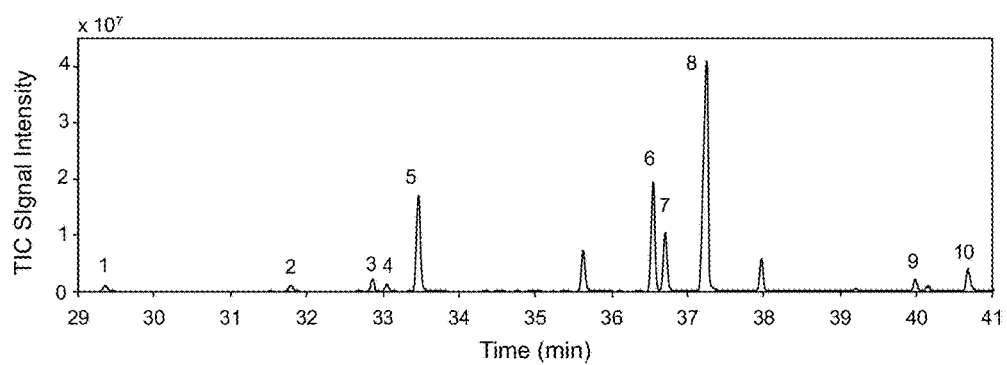
FIG. 11 shows a GC-MS Total Ion Chromatograph of thermally depolymerized mcl-PHAs.

To demonstrate production of chemical precursors from lignin, depolymerization of the mcl-PHAs was conducted. Thermal decomposition at 250° C. was employed, which results in dehydration and a monomer distribution reflective of the parent polymer (FIG. 11, Table 2). These lignin-derived monomeric acids can subsequently be upgraded via known catalytic routes to produce petrochemical substitutes.

Recovered mcl-PHAs were thermally depolymerized to produce free acid monomers for catalytic upgrading. Thermal depolymerization was performed using a Parr 5000 Multireactor, outfitted with 75-mL reactor vessels. The reactor vessel was loaded with 445 mg of recovered PHA and purged with Ar for three cycles. The gas purge line was then closed, and the reactor was heated to 250° C. for 30 min at temperature (CITE if possible). The depolymerization products were recovered in dichloromethane, filtered (0.2-μm PTFE), and quantified by GC-MS, as described above. Depolymerized acid standards (i.e., 3-hydroxyoctanoic acid, 3-hydroxydecanoic acid, 3-hydroxydodecanoic acid, octenoic acid, decenoic acid) were obtained from Sigma-Aldrich. FIG. 11 shows the results of this analysis, with the identified peaks delineated in Table 2 below.

TABLE 2

| Peak No. | RT (min) | Catalytic Deoxygenation Species |
|---|---|---|
| 1 | 29.4 | 2-Hexenoic acid |
| 2 | 32.9 | 3-Octenoic acid |
| 3 | 33.1 | 2-Octenoic acid |
| 4 | 33.5 | 2-Octenoic acid |
| 5 | 36.5 | 3-Decenoic acid |
| 6 | 36.7 | 3-Decenoic acid |
| 7 | 37.3 | 2-Decenoic acid |
| 8 | 40.0 | 1-Tetradecene |
| 9 | 40.2 | 5-Dodecenoic acid |
| 10 | 40.7 | 2-Dodecenoic acid |

Example 13

Catalytic Upgrading and Product Analysis

As a final demonstration of lignin valorization, recovered mcl-PHAs were converted to hydrocarbon fuels by tandem thermal depolymerization and catalytic deoxygenation (FIG. 3C, right panel). Depolymerized acids were converted to hydrocarbons over a platinum-rhenium catalyst supported on activated carbon via reduction and decarboxylation-decarbonylation at 300° C. using water as a solvent under mild hydrogen pressure (2.5 MPa initial $H_2$ loading) (FIGS. 3A,C). The use of water as a solvent facilitates reforming of renewable $H_2$-donors in situ, while CO produced from decarbonylation can react with water to produce $H_2$ via the water gas shift reaction, minimizing external $H_2$ requirements. The distribution of alkanes was reflective of the hydroxyacid monomer decarboxylation/decarbonylation, and a novel demonstration for conversion of lignin-derived mcl-PHAs to a "drop-in" biofuel (FIG. 12; Table 3).

Depolymerized PHAs recovered from *P. putida* were catalytically converted to hydrocarbons over Pt—Re/C using water as a solvent. Pt—Re/C (5 wt % Pt, 4 wt % Re) was prepared by aqueous adsorption of Re onto commercial Pt/C, followed by in situ reduction at 200° C. Catalytic conversion of depolymerized PHAs was conducted using the Parr 5000 Multireactor described above. The 75-mL reactor vessel was loaded with 175 mg of depolymerized PHA, 50 mg of Pt—Re/C, and 9.8 mL of deionized water. Prior to conversion, the vessels were purged with Ar for three cycles, and pressurized to 2.75 MPa with $H_2$ at ambient temperature. The reactors were then heated to 300° C. under rapid stirring for 180 minutes at temperature. The catalytic upgrading products were recovered in dichloromethane, filtered (0.2-μm PTFE), and quantified by GC-MS, as described above. Mixed hydrocarbon standards were obtained from Sigma-Aldrich.

Figure 12:
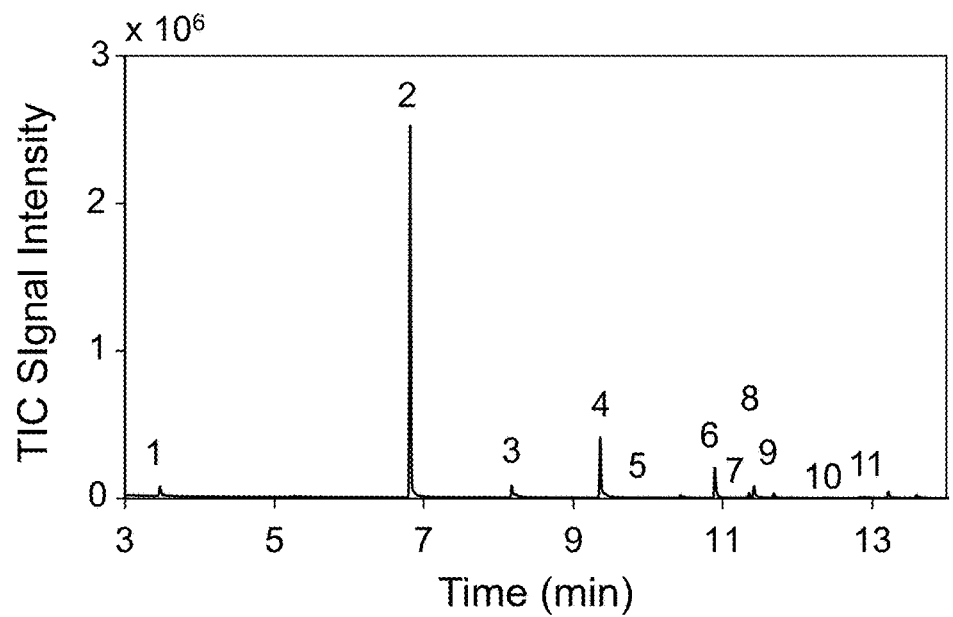
FIG. 12 shows a GC-MS Total Ion Chromatograph of thermally depolymerized and catalytically deoxygenated mcl-PHAs.
Figure 12:
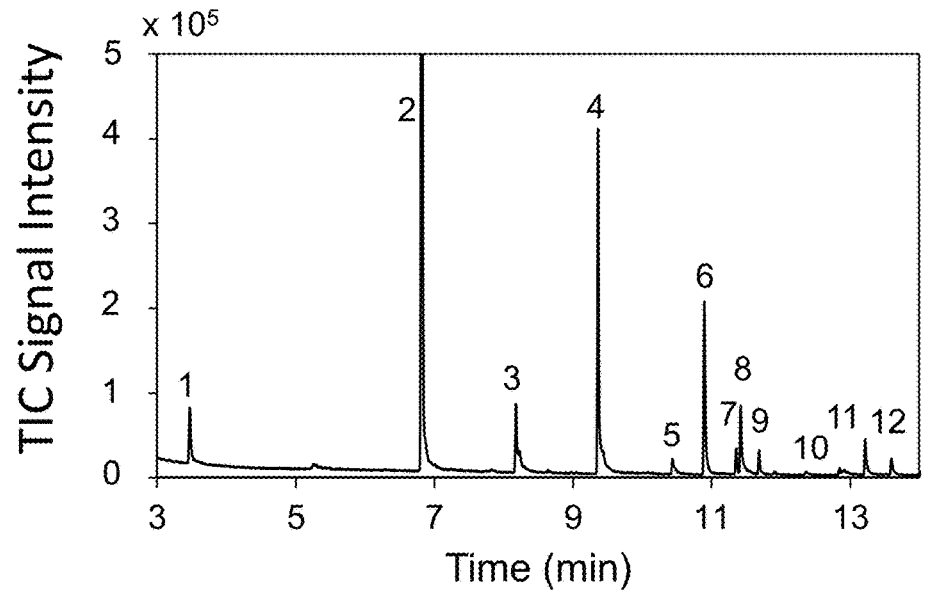

Table 3 list compounds identified by GC-MS from the catalytic deoxygenation of thermally depolymerized PHAs corresponding to the chromatograph shown in FIG. 12. Compound response factors for linear alkanes were determined by mixed standards.

TABLE 3

| Peak No. | RT (min) | Compound Name |
|---|---|---|
| 1 | 3.4 | Heptane |
| 2 | 6.8 | Nonane |
| 3 | 8.2 | Decane |
| 4 | 9.4 | Undecane |
| 5 | 10.4 | Dodecane |
| 6 | 10.9 | Cyclic hydrocarbon |
| 7 | 11.3 | Cyclic hydrocarbon |
| 8 | 11.4 | Tridecane |
| 9 | 11.7 | Cyclic hydrocarbon |
| 10 | 12.3 | Tetradecane |
| 11 | 12.9 | Cyclic hydrocarbon |
| 12 | 13.6 | Branched hydrocarbon |

We claim:

1. A method comprising:
   treating a solid lignocellulosic biomass with an alkaline compound to produce a lignin liquor phase and a residual solid polysaccharide phase,
   wherein the lignin liquor phase comprises lignin with aromatic components; and
   a first culturing of the lignin liquor phase with a bacterium from the genus *Pseudomonas* that converts at least a portion of the aromatic components to produce a polyhydroxyalkanoate (PHA).

2. The method of claim 1, further comprising, before the first culturing:
   separating at least a portion of the lignin liquor phase from the residual solid polysaccharide phase, wherein:
   the separated lignin liquor phase is substantially free of the residual solid polysaccharide phase, and
   the separated residual solid polysaccharide phase is substantially free of the lignin liquor phase.

3. The method of claim 2, wherein the separating is performed by filtration.

4. The method of claim 3, further comprising incubating the separated residual solid polysaccharide phase with a cellulase enzyme to produce sugars.

5. The method of claim 4, further comprising fermenting the sugars to a biofuel by a second culturing of the sugars with an organism.

6. The method of claim 1, further comprising heating the PHA, wherein the heating depolymerizes at least a portion of the PHA to a hydroxyacid.

7. The method of claim 6, further comprising converting at least a portion of the hydroxyacid to a hydrocarbon by treating at least a portion of the hydroxyacid with a bimetallic catalyst.

8. The method of claim 7, wherein the bimetallic catalyst comprises a noble metal.

9. The method of claim 8, wherein the noble metal comprises at least one of platinum or rhenium.

10. The method of claim 7, wherein the converting is carried out in an aqueous solvent.

11. The method of claim 1, wherein the solid lignocellulosic biomass comprises corn stover.

12. The method of claim 1, wherein the bacterium comprises a species of *P. putida*.

13. The method of claim 12, wherein the bacterium comprises *P. putida* KT2440.

14. The method of claim 1, wherein the alkaline compound comprises sodium hydroxide.

15. The method of claim 1, wherein the treating is performed using a redox catalyst.

16. The method of claim 15, wherein the redox catalyst comprises anthraquinone.

* * * * *